(12) United States Patent
Vessey et al.

(10) Patent No.: US 7,943,331 B2
(45) Date of Patent: May 17, 2011

(54) WHOLE BLOOD ASSAY

(75) Inventors: John Phillip Vessey, East Horsley (GB); Adrian Richard Gray, Wokingham (GB); David Percival, Hawarden (GB)

(73) Assignee: Quotient Diagnostics Limited, Walton on Thames, Surrey (GB)

( * ) Notice: Subject to any disclaimer, the term of this patent is extended or adjusted under 35 U.S.C. 154(b) by 0 days.

(21) Appl. No.: 12/532,596

(22) PCT Filed: Mar. 20, 2008

(86) PCT No.: PCT/GB2008/050204
§ 371 (c)(1),
(2), (4) Date: Nov. 23, 2009

(87) PCT Pub. No.: WO2008/114060
PCT Pub. Date: Sep. 25, 2008

(65) Prior Publication Data
US 2010/0075338 A1    Mar. 25, 2010

(30) Foreign Application Priority Data
Mar. 22, 2007  (GB) .................................. 0705495.0

(51) Int. Cl.
*G01N 31/00*   (2006.01)
*G01N 33/53*   (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search ........................ None
See application file for complete search history.

(56) References Cited

U.S. PATENT DOCUMENTS
2005/0267346 A1   12/2005   Faber et al.
2006/0281187 A1   12/2006   Emery et al.

FOREIGN PATENT DOCUMENTS
EP   1037048 A2   9/2000
EP   1467206 A1   10/2004
EP   1486778 A2   12/2004
WO   WO0157510 A2   8/2001

*Primary Examiner* — Lisa V Cook

(57) ABSTRACT

A method and apparatus to estimate the concentration of a target substance (e.g. Cholesterol or CRP) in the plasma component of awhole blood sample without the need to separate the red blood cells from the plasma prior to testing, thereby simplifying the design and construction of the test device. The invention achieves this by measuring the analyte under investigation in a time dependent (bio-/immuno-) chemical reaction and measuring separately, a marker substance (e.g haemoglobin) for the estimation of red blood cell volume, using a non-time-dependent alteration in physical property of the reaction mixture (in this instance, transmission) attributed to inherent filter effects on sample addition. These non-time-dependent changes are not part of the reaction chemistry, and are resolved from the time dependent alteration in physical property caused by the assay chemistry by continuous measurement and mathematical modelling. Algorithms that combine these two parameters are used to estimate the target substance and compensate for variations in the percentage haematocrit of the sample. The method equalises the assay response for subtle variations in patient sample (e.g. haematocrit).

17 Claims, 3 Drawing Sheets

WHOLE BLOOD ASSAY

CROSS REFERENCE TO RELATED APPLICATIONS

This application is the National Stage entry of PCT/GB2008/050204, filed Mar. 20, 2008, which claims priority to British application number 0705495.0, filed Mar. 22, 2007, both of which are incorporated herein by reference in their entireties.

The present invention relates to methods of carrying out an assay for a substance in a whole blood sample.

UK patent application number 0606450.5 describes the assay of glycated proteins by fluorescence quenching using a method and apparatus to estimate the concentration of a non-fluorescent substance (e.g. haemoglobin) in a fluorescent assay by separately estimating the non-time-dependent alteration attributed to inherent filter effects from the time dependent alteration caused by the assay chemistry (measuring haemoglobin-A1c). Such a method obviates the requirement for a separate photometric or other measurement thereby simplifying the methodology and associated instrumentation.

The present invention is an adaptation of this approach for the measurement of other substances, not necessarily by fluorimetry, whereby the developing signal (e.g. transmission) is monitored continuously and used, not only to measure the substance undergoing reaction, but also to measure and compensate for the initial amount of sample added.

The prior art involves the assay of a range of substances whereby a specific reaction chemistry is followed photo-metrically with time, for example by utilising an antibody specific to an analyte that is coated onto microfine latex particles and measuring the increased turbidity that is produced when the analyte being measured promotes aggregation of the latex particles as the reaction between analyte/antigen and antibody proceeds. This measurement of increasing turbidity can be achieved using a conventional photometer and using the associated scientific principles of photometric measurements. Such concentration dependent turbidity is then compared to that produced by standards which is established prior art.

Further compatible methodologies include carrying out a series of enzyme-linked reactions in solution, where an analyte in the plasma fraction of a whole blood sample is altered by an enzyme-promoted reaction to ultimately derive a coloured dye from colourless reaction constituents. The colour is developed in a time dependent way and monitored photometrically. This measurement of colour change can also be achieved using a conventional photometer using the associated scientific principles of photometric measurements. Such concentration dependent change in transmission is then compared to that produced by standards which method is also established prior art.

In whole blood samples there is a variable which must be taken into account when analysing substances that are present in the plasma component. This is the haematocrit or percentage of red blood cells by volume in the whole blood sample and this value can vary widely depending on age, climate, nutritional and disease status and other factors. For example, a 40% haematocrit means that in a given volume of whole blood, 40% of that volume is attributed to the volume taken up by red blood cells and 60% to plasma. As the haematocrit of a patient's blood rises, so the volume of plasma in a fixed volume sample which is introduced into the test device decreases and vice versa. Since it is the plasma component which exclusively carries the analyte being measured, then the lower the volume of plasma component added to the reaction mix, the lower the resulting concentration of the substance being measured in that reaction mix and the resulting assayed value and vice versa.

Any analysis that produces a concentration of a plasma substance in whole blood must be corrected for variations in haematocrit to give a true plasma concentration. It is for this reason that such assays are conventionally performed on serum or plasma that has been separated previously from red blood cells by filtration or centrifugation. In a point of care, doctor's office or clinic setting, small volumes of whole blood sample may be separated from the plasma component by filtration or other mechanical manipulations which add complexity, and hence cost, into the design of the system.

It would be most useful in these situations to measure two substances, one of which is the analyte under investigation and the other which is considered to be a marker by which to estimate or normalise the sample haematocrit.

It is known that the haemoglobin concentration of whole blood, after red blood cells are lysed, is directly proportional to the red blood cell volume in the whole blood sample.

Haemoglobin concentration can be estimated photometrically by known means at various wavelengths or by various reaction chemistries as described above (i.e. turbidity or enzyme-catalysed colour formation). An instrument that measures transmission of a sample continuously, after allowing for the necessary blanking measurements initially, at a point in the visible spectrum where both assay chemistry (either colour formation or development of turbidity) and haemoglobin can be measured may, by the use of the algorithms described in UK patent application 0606450.5, make estimates of the initial transmission, and hence derive an estimate of haemoglobin concentration (since this effect is instantaneous and not dependent on any chemical reaction) before the analyte reaction chemistry progresses. The same algorithm also makes a measurement of the final transmission which would, by differential analysis, represent the time dependent chemistry undergone by the analyte under investigation. An algorithm that computes the relationship between these two estimates may be used to produce a plasma value that is not influenced by variations in haematocrit.

According to a first aspect of the present invention there is provided a method of carrying out an assay for substance in a sample of whole blood, which method comprises:

(a) carrying out a reaction in solution between an analyte in the whole blood sample and a specific reagent, the sample being combined with the reagent at time $t_0$;

(b) monitoring the transmission of the solution continuously as the reaction progresses at a suitable wavelength;

(c) recording, from the detected transmission values, the transmission, $T_{init}$, being the transmission of the reaction solution before the addition of the sample; and calculating $T_0$, being the transmission at time $t_0$ after the sample has been added and $T_\infty$ being the transmission at time $t_\infty$, which is the point at which all of the analyte has reacted with the reagent, or has attained equilibrium;

(d) calculating from the values of $T_{init}$ and $T_0$ the optical density of the sample after blood addition and hence quantity of haemoglobin added in that sample;

(e) calculating from the values of $T_0$ and $T_\infty$ the change in transmission attributable to the reaction in step (a); and (f) deriving from the relationship between these measurements the concentration of the analyte in the sample, corrected for haematocrit variation.

A currently intended major use of the present invention is in the assaying of plasma analytes in whole blood. Two examples are described below to illustrate the principles applied to the measurement of an analyte such as C-reactive Protein (CRP) by an immunoturbidimetric method, or to a different analyte such as cholesterol by a series of enzyme driven linked reactions to produce a coloured end point.

In the immunoturbidimetric example, preferably the antibody to CRP is bound to a particle, such as a latex bead, that will aggregate as the reaction between antibody and analyte progresses.

In the enzyme-driven series of linked reactions, preferably the key enzymes are specific to the substance being measured such as cholesterol esterase and cholesterol oxidase.

The relationship derived from the measurements of $T_0$ and $T_\infty$ referred to in step (f) will preferably be achieved using an algorithm of the form:

$$y=ax^2+bx+c$$

where a, b and c are calibration constants, y is a measure of analyte chemistry e.g. $\log [(T_0-T_\infty)/T_0]$ and x is a measure of haemoglobin e.g. $\log [(T_{init}-T_0)/T_{init}]$.

In a fully automated instrument system, where blood is added to the reagent and mixed by the instrument, the earliest transmission point detectable as the reaction chemistry progresses might possibly be determined within the first 5 seconds or so after blood addition and mixing. However, in a non-automated system, the monitoring of the initial binding reaction is further delayed due to the finite time required by an operator physically to add the blood specimen to the reaction cuvette containing the reagent, then mix and return the reaction cuvette to the photometer. Therefore, the actual transmission level at $t_0$, immediately after the addition of the blood specimen, cannot directly be measured in either the manual or automatic system.

To overcome this, the transmission level $T_0$ at time $t_0$ i.e. immediately after sample addition and mixing but before reaction has occurred, is preferably determined by back extrapolation of a curve fitted to the time course transmission data, based upon the rate equation of the chemical binding reaction. This, preferably, includes plotting the detected transmission data against time, and applying a best fit curve to the plotted points. The plotting may be physical or even manual, but is often achieved automatically and mathematically by fitting a mathematical function of a curve of best fit to the data and extrapolating that function to time $t_0$ and $t_\infty$, without the generation of a graph as such. The curve fitting may be achieved by any suitable mathematical method, and an example method is described later in this specification. Using these regimes the recorded data is used to minimise variance and then the curve is extrapolated to provide values for $T_0$.

Further, by forward extrapolation of this curve fit beyond the data collection period, the transmission level $T_\infty$ at time $t_\infty$, the reaction end-point, is also determined. Determining the transmission levels at $t_0$ and $t_\infty$ in this manner has been found to produce reliable and accurate results.

The time period over which the transmission of the reaction mixture is measured may be anything suitable for the use to which the assay is put. A long period gives greater accuracy, but a slower assay process; whereas a short period is convenient, but may lead to less precise results as the amount of data from which to extrapolate becomes sparse. The suitable length of the measurement period will depend on the substance being assayed and the time profile of its reaction with the antibody. In respect of both the CRP immunoturbidimetric assay and the enzymatic cholesterol assay using readily available reagents, a measurement period of about 3 minutes is usually appropriate. It is also possible to shorten the time period by extrapolating the results from less data and continually checking the accuracy of the extrapolation as the reaction progresses. If the data from early extrapolation (i.e. a short period such as 20-30 seconds) is being substantiated by the continuing recorded observation, the original extrapolation may be used to reliably predict the end point and start point result from less data and in a shorter period of time.

It is preferred that before the sample is combined with the antibody reagent in step (a), the solution alone is excited by incident electromagnetic radiation of a suitable wavelength $\lambda_n$ (i.e. a wavelength where transmission measurements can detect both haemoglobin and either the turbidity produced by the antibody-analyte reaction or the colour produced by the enzyme driven linked reactions) and the resultant initial transmission ($T_{init}$) at the selected wavelength frequency is detected. This in combination with the value of $T_0$ can be used to calculate the Zero Optical Density (ZOD) using the equation:

$$ZOD=\log [T_{init}/T_0]$$

The ZOD is known to be directly proportional to the total haemoglobin concentration. The measurement of initial transmission can therefore be used to determine total haemoglobin concentration, which, in turn, may be used to determine red blood cell volume.

It may not be necessary to determine $T_{init}$ before every assay, as this value may be a standard or constant value depending on the reproducibility of the reaction cuvette and the reagents used.

Many modifications of the methods and apparatus of the present invention described herein will be apparent to the skilled man and these fall within the scope of the present invention. Fundamental to the invention however is that the physical parameter being measured (be it fluorescence, transmission or some other physical property such as turbidity) is altered in a time dependent fashion by the specific reaction of one substance on the one hand and in an instantaneous, and therefore non-time dependent, fashion by another substance on the other; one substance being the target analyte being measured, another substance being the marker by which variations in sample addition or property are compensated for.

However in order that its principles may be better understood, but by way of example only, the present invention will now be described in detail with reference to the example of measuring cholesterol in whole blood and where appropriate to the accompanying drawings in which.

Figure 5:
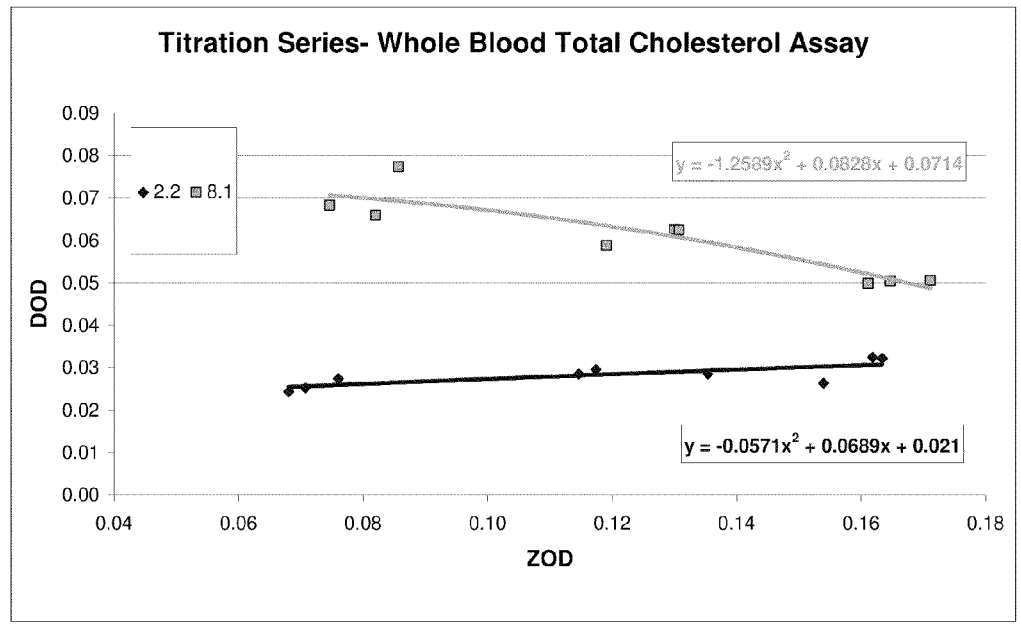
Figure 6:
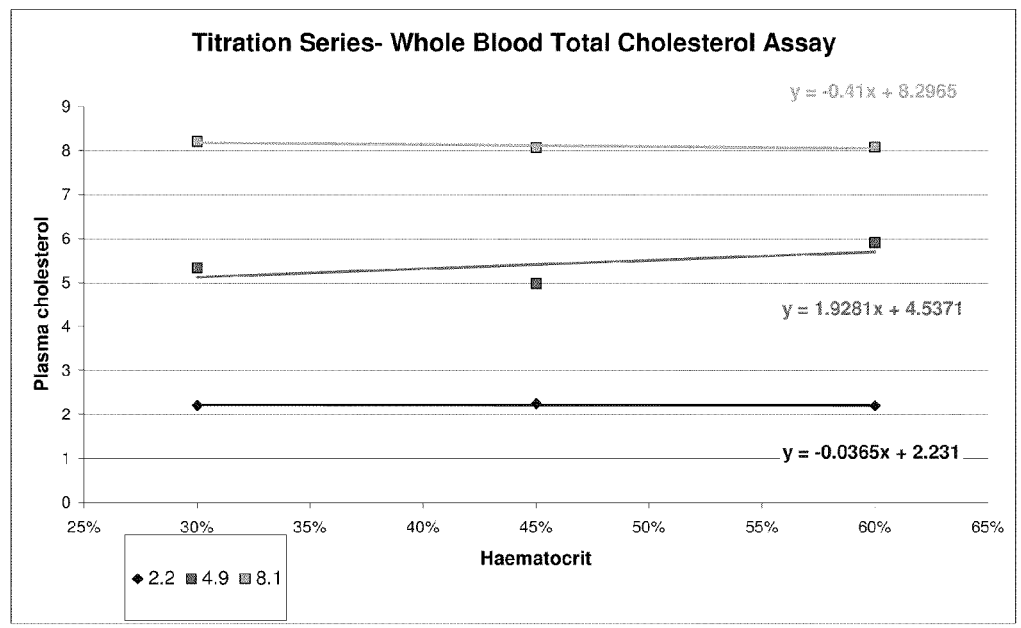

FIG. 5 shows the relationship between the Delta Optical Density (DOD), being the difference between $OD_0$ and $OD_\infty$ of the reaction chemistry, and Zero Optical Density (ZOD), being the measure of haemoglobin (and hence haematocrit), for a low (2.2 mmol/litre) and high (8.1 mmol/litre) standard blood sample; and FIG. 6 shows the cholesterol values derived from the algorithm and reaction chemistry method as they vary with sample haematocrit for three standards covering the assay working range.

The present invention may be used to assay cholesterol in blood. In such a method the constituents of a series of enzyme-linked reactions dissolved in a suitable buffer are introduced into a cuvette. Prior to the introduction of a blood specimen, this reagent mixture is excited in a photometer by EM radiation at a suitable wavelength (510 nm) and the transmission blank ($T_{Init}$) is measured.

Figure 1:
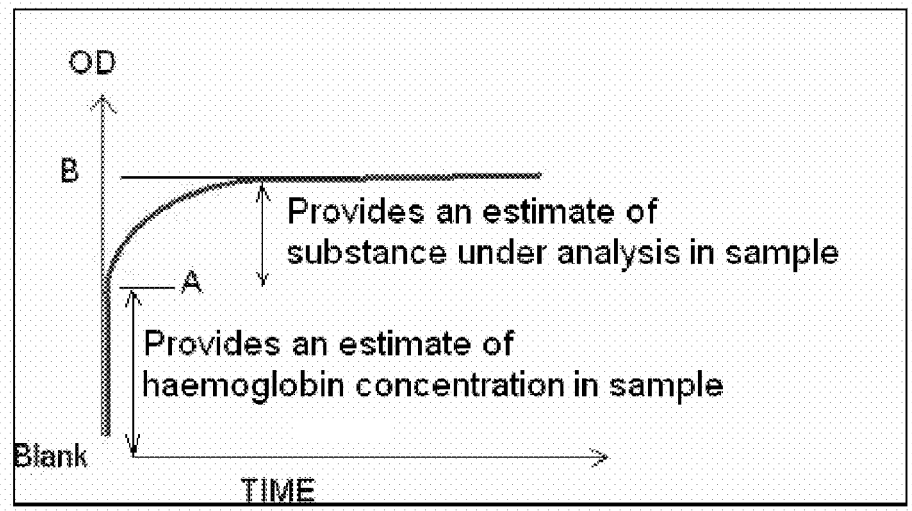
FIG. 1 is a graph of a general profile of a reaction in which Optical Density (OD) increases due to the specific reaction chemistry as reaction time progresses after an initial increase in OD (or drop in transmission) attributed to the presence of the sample itself after initial blank measurement.
Figure 2:
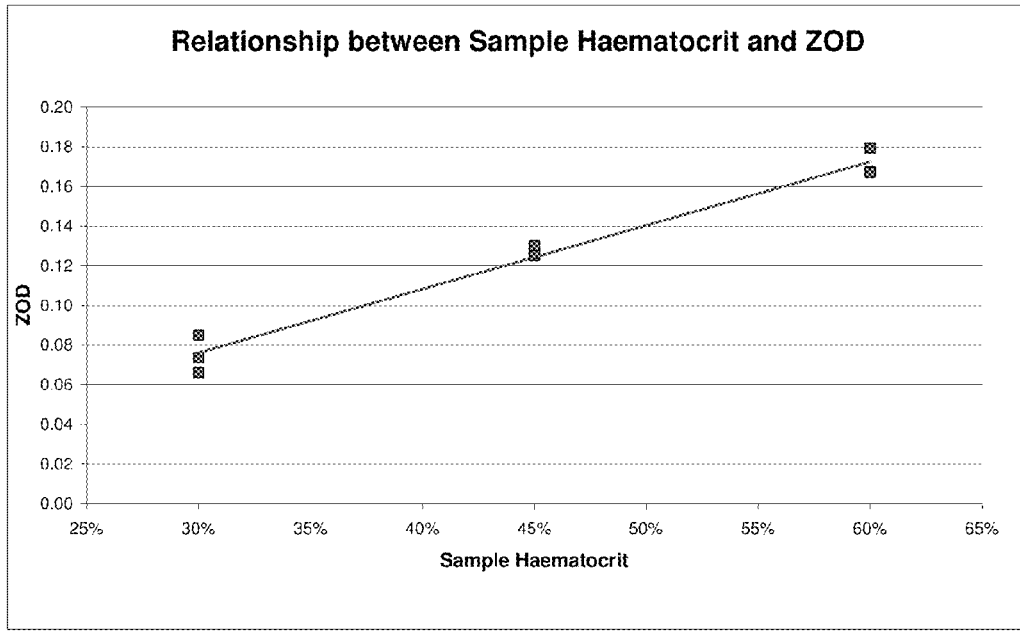
FIG. 2 is a graph depicting the relationship between Zero Optical Density (ZOD) at 510 nm derived from the initial drop in transmission (i.e. at time zero) and quantity of haemoglobin (from a fixed volume of sample at varying haematocrit levels) added.
Figure 3:
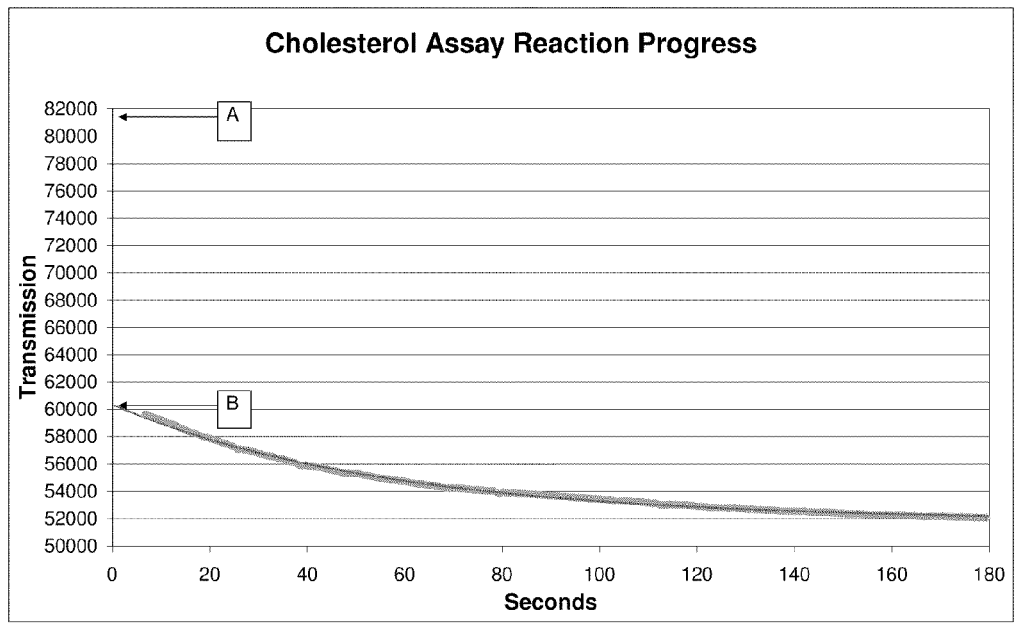
FIG. 3 is a plot of the transmission signal time course during the development of a coloured response in solution from cholesterol in the sample and a series of enzyme-linked reactions that alter a colourless precursor into a coloured dye.
Figure 4:
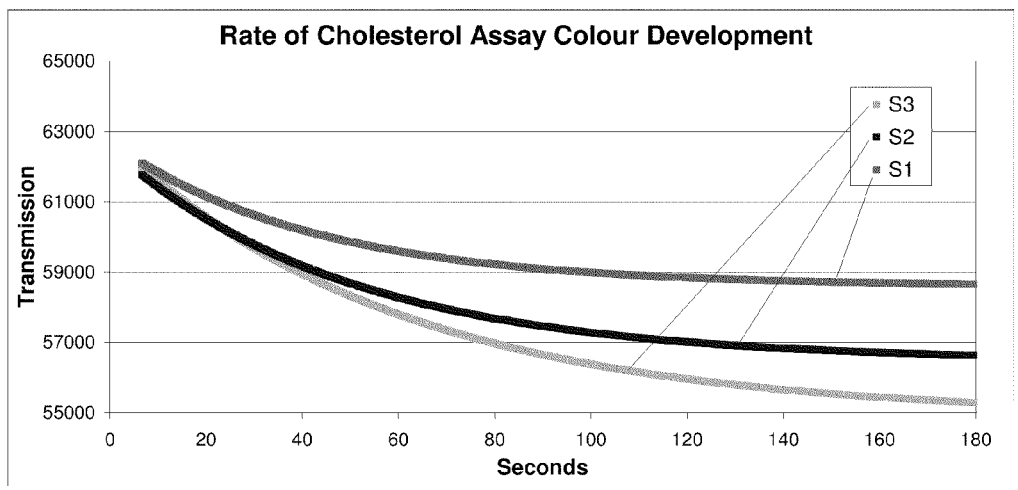
FIG. 4 is a composite plot of the time course of reduction in transmission during the reaction between various levels of cholesterol in solution and a series of cholesterol-specific, enzyme-linked reactions in the presence of blood.

The cuvette is removed from the photometer or left in place and the blood sample is immediately added and mixed and the transmission over a time course is detected and recorded. This data is plotted and a curve is fitted to the data set. FIG. 3 shows such a reaction time profile where the initial transmission $T_{Init}$ labelled A is recorded prior to sample introduction at zero seconds. The actual experimental transmission data for the reaction is recorded over time (usually at less than 1 second intervals) from the reintroduction of the cuvette in a manual system or after mixing in an automatic system until a suitable period has elapsed. By back extrapolation, the transmission level $T_0$ is determined at $t_0$, i.e. the point when the sample was added but no reaction with the target analyte had occurred (B). By forward extrapolation (which is not shown because the end of the measured data is off the graph in FIG. 3) the transmission level $T_\infty$ at the reaction end-point $t_\infty$ is similarly determined wherein the reaction with the target analyte has attained completion.

Of many potential curve fit routines that have been shown to be effective in the extrapolated estimation of $T_0$ and $T_\infty$ a suitable curve fitting routine is based upon the general rate equation below:

$$T_t = T_0 + (T_\infty - T_0) \times (1 - e^{-t/\theta})$$

where,
$T_t$=Transmission at time t seconds
$T_0$=Transmission at time zero
$T_\infty$=Transmission at time infinity (i.e. at reaction end)
e=2.7813 (natural log base)
θ=rate constant with $T_0$, $T_\infty$ and θ being determined iteratively by minimising the sum of the squared variances between the fitted and measured value at each one second data point. i.e. $\Sigma (T_{t\text{-}actual} - T_{t\text{-}estimated})^2$ is minimised by the fitting routine.

The mathematical modelling of the data can be achieved by other methods of curve fitting which may be equally acceptable in practice.

EXAMPLE

A known volume (e.g. 2.0 ml) of reagent comprising a buffer and a mixture of enzyme and reactants for the enzyme-linked reactions (see below) was introduced into a reaction cuvette.

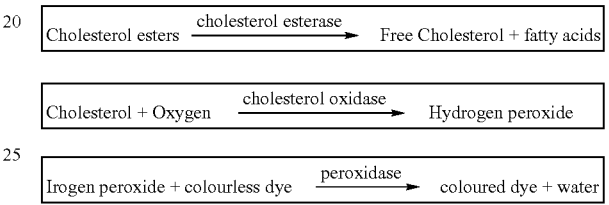

This mixture was introduced into a photometer and was excited at 510 nm. Blank transmission readings were taken at <1 second intervals for about five seconds.

A fixed volume (5 μL) of blood, whose plasma cholesterol level was known, was then introduced into the cuvette at time $t_0$ and mixed. When the mixing ceased the transmission at 510 nm was then measured for 3 minutes reaction time. The time taken to effect mixing and for the vortex in the liquid to stop means that the transmission was only recorded from about the 10th second after the addition of the blood sample onwards.

An example of the blank and blood readings of transmission signal and reference are laid out in Table 1 below.

TABLE 1

| Reading time | Transmission |
|---|---|
| 0.42 | 81679 |
| 0.79 | 81715 |
| 1.16 | 81729 |
| 1.52 | 81736 |
| 1.89 | 81731 |
| 2.26 | 81740 |
| 2.63 | 81722 |
| 2.99 | 81734 |
| 3.36 | 81729 |
| 3.73 | 81761 |
| 4.1 | 81776 |
| 4.47 | 81785 |
| 4.83 | 81779 |
| 5.2 | 81773 |

| Column 1 Time after blood addition (secs) | Column 2 T | Column 3 Mathematically fitted curve | Column 4 Time after blood addition (secs) | Column 5 T | Column 6 Mathematically fitted curve | Column 7 Time after blood addition (secs) | Column 8 T | Column 9 Mathematically fitted curve |
|---|---|---|---|---|---|---|---|---|
| 0.42 | | 56090 | 60.36 | 49933 | 50023 | 120.29 | 47761 | 47798 |
| 1.16 | | 55972 | 61.09 | 49901 | 49980 | 121.03 | 47713 | 47782 |
| 2.26 | | 55799 | 62.2 | 49905 | 49916 | 122.13 | 47614 | 47759 |
| 3.36 | | 55630 | 63.3 | 49823 | 49854 | 123.24 | 47600 | 47736 |
| 4.47 | | 55462 | 64.4 | 49757 | 49793 | 124.34 | 47618 | 47714 |
| 5.57 | | 55299 | 65.51 | 49683 | 49732 | 125.44 | 47574 | 47692 |

TABLE 1-continued

| | | | | | | | | |
|---|---|---|---|---|---|---|---|---|
| 6.67 | | 55138 | 66.61 | 49643 | 49674 | 126.55 | 47575 | 47670 |
| 7.41 | | 55032 | 67.34 | 49598 | 49635 | 127.28 | 47552 | 47656 |
| 8.14 | | 54928 | 68.08 | 49594 | 49597 | 128.02 | 47510 | 47642 |
| 9.25 | | 54774 | 69.18 | 49525 | 49540 | 129.12 | 47530 | 47621 |
| 10.35 | 54801 | 54623 | 70.29 | 49469 | 49485 | 130.22 | 47520 | 47601 |
| 11.08 | 54610 | 54524 | 71.02 | 49452 | 49449 | 130.96 | 47566 | 47587 |
| 12.19 | 54594 | 54377 | 72.12 | 49427 | 49395 | 132.06 | 47652 | 47568 |
| 13.29 | 54443 | 54233 | 73.23 | 49413 | 49342 | 133.17 | 47690 | 47548 |
| 14.06 | 54352 | 54134 | 73.96 | 49372 | 49307 | 133.9 | 47755 | 47536 |
| 15.13 | 54200 | 53999 | 75.07 | 49296 | 49256 | 135 | 47781 | 47517 |
| 16.23 | 53996 | 53862 | 76.17 | 49296 | 49206 | 136.11 | 47774 | 47498 |
| 17.34 | 53869 | 53727 | 77.27 | 49223 | 49157 | 137.21 | 47754 | 47480 |
| 18.44 | 53678 | 53595 | 78.38 | 49181 | 49108 | 138.31 | 47729 | 47463 |
| 19.91 | 53449 | 53423 | 79.85 | 49134 | 49045 | 139.78 | 47688 | 47440 |
| 20.64 | 53331 | 53339 | 80.58 | 49087 | 49014 | 140.52 | 47694 | 47428 |
| 21.75 | 53242 | 53213 | 81.69 | 49017 | 48968 | 141.62 | 47690 | 47411 |
| 22.85 | 53125 | 53091 | 82.79 | 49028 | 48923 | 142.73 | 47676 | 47395 |
| 23.95 | 52990 | 52971 | 83.89 | 48979 | 48879 | 143.83 | 47608 | 47379 |
| 25.06 | 52862 | 52852 | 85.01 | 48916 | 48835 | 144.93 | 47539 | 47363 |
| 26.16 | 52736 | 52736 | 86.1 | 48938 | 48793 | 146.04 | 47457 | 47347 |
| 27.29 | 52620 | 52620 | 87.2 | 48945 | 48751 | 147.14 | 47258 | 47332 |
| 28 | 52509 | 52548 | 87.94 | 48871 | 48724 | 147.87 | 47088 | 47322 |
| 29.1 | 52405 | 52437 | 89.04 | 48896 | 48683 | 148.98 | 47030 | 47307 |
| 30.21 | 52275 | 52328 | 90.14 | 48874 | 48644 | 150.08 | 47152 | 47292 |
| 30.57 | 52252 | 52293 | 90.51 | 48867 | 48631 | 150.45 | 47218 | 47287 |
| 31.31 | 52170 | 52222 | 91.25 | 48835 | 48604 | 151.18 | 47278 | 47278 |
| 32.78 | 52016 | 52083 | 92.72 | 48777 | 48554 | 152.65 | 47313 | 47259 |
| 33.15 | 51954 | 52049 | 93.08 | 48775 | 48541 | 153.02 | 47277 | 47255 |
| 34.99 | 51684 | 51881 | 94.92 | 48731 | 48480 | 154.86 | 46858 | 47232 |
| 35.35 | 51650 | 51849 | 95.29 | 48740 | 48468 | 155.23 | 46763 | 47228 |
| 36.82 | 51545 | 51719 | 96.76 | 48708 | 48420 | 156.7 | 46498 | 47210 |
| 37.93 | 51428 | 51623 | 97.86 | 48600 | 48385 | 157.8 | 46318 | 47197 |
| 38.3 | 51405 | 51592 | 98.24 | 48586 | 48373 | 158.17 | 46304 | 47193 |
| 39.77 | 51196 | 51468 | 99.7 | 48508 | 48328 | 159.64 | 46324 | 47177 |
| 40.13 | 51140 | 51438 | 100.07 | 48493 | 48317 | 160.01 | 46370 | 47172 |
| 41.97 | 51052 | 51289 | 101.91 | 48376 | 48262 | 161.85 | 46584 | 47152 |
| 42.34 | 51056 | 51259 | 102.28 | 48326 | 48251 | 162.21 | 46638 | 47149 |
| 43.81 | 50925 | 51144 | 103.75 | 48292 | 48209 | 163.69 | 46544 | 47133 |
| 44.18 | 50903 | 51115 | 104.12 | 48260 | 48199 | 164.05 | 46487 | 47129 |
| 45.65 | 50775 | 51003 | 105.59 | 48302 | 48157 | 165.52 | 46519 | 47114 |
| 46.02 | 50673 | 50976 | 105.95 | 48304 | 48148 | 165.89 | 46544 | 47110 |
| 47.86 | 50253 | 50840 | 107.79 | 48278 | 48098 | 167.73 | 46587 | 47092 |
| 48.22 | 50203 | 50814 | 108.16 | 48281 | 48088 | 168.1 | 46549 | 47089 |
| 49.69 | 50152 | 50709 | 109.63 | 48247 | 48050 | 169.57 | 46668 | 47074 |
| 50.06 | 50096 | 50684 | 110 | 48268 | 48040 | 169.94 | 46677 | 47071 |
| 51.9 | 49943 | 50557 | 111.84 | 48246 | 47994 | 171.77 | 46680 | 47054 |
| 52.27 | 49926 | 50532 | 112.21 | 48230 | 47985 | 172.14 | 46674 | 47051 |
| 53.74 | 50013 | 50434 | 113.68 | 48199 | 47949 | 173.61 | 46724 | 47038 |
| 54.11 | 50035 | 50410 | 114.04 | 48193 | 47940 | 173.98 | 46768 | 47034 |
| 55.95 | 50102 | 50292 | 115.88 | 48074 | 47897 | 175.82 | 46703 | 47018 |
| 56.31 | 50115 | 50269 | 116.28 | 48036 | 47888 | 176.19 | 46694 | 47015 |
| 57.78 | 50095 | 50178 | 117.72 | 47976 | 47855 | 177.66 | 46730 | 47003 |
| 58.15 | 50087 | 50155 | 118.09 | 47967 | 47846 | 178.03 | 46751 | 47000 |
| 59.99 | 49959 | 50044 | 119.93 | 47794 | 47806 | 179.86 | 46780 | 46985 |
| 60.36 | 49933 | 50023 | 120.29 | 47761 | 47798 | 180.23 | 46774 | 46982 |

Columns 2, 4, 6 and 8 are the measured transmission readings. If this data is plotted against time it produces a curve as shown in FIG. 3. A mathematically derived curve is fitted to these values using a suitable algorithm as previously discussed and the values (as shown in columns 3, 5, 7 and 9) are also plotted on the graph in FIG. 3. The values $T_0$ and $T_\infty$ can be derived for this sample by back and forward extrapolation of the data fit to $t_0$ and $t_\infty$ respectively.

Table 2 shows the results of a series of equivalent assays run on blood samples where the haematocrit has been deliberately manipulated to cover the normal range of 30% to 60%.

TABLE 2

| Column 1 Cholesterol Target | Column 2 Haematocrit | Column 3 ZOD | Column 4 DOD | Column 5 Cholesterol calculated | Column 6 Mean | Column 7 CV |
|---|---|---|---|---|---|---|
| 2.2 | 30% | 0.068 | 0.024 | 2.06 | 2.21 | 7.91% |
| 2.2 | 30% | 0.076 | 0.027 | 2.40 | | |
| 2.2 | 30% | 0.071 | 0.025 | 2.16 | | |
| 2.2 | 45% | 0.117 | 0.030 | 2.41 | 2.24 | 7.74% |
| 2.2 | 45% | 0.115 | 0.029 | 2.26 | | |
| 2.2 | 45% | 0.135 | 0.029 | 2.06 | | |
| 2.2 | 60% | 0.163 | 0.032 | 2.63 | 2.20 | 37.37% |

TABLE 2-continued

| Column 1 Cholesterol Target | Column 2 Haematocrit | Column 3 ZOD | Column 4 DOD | Column 5 Cholesterol calculated | Column 6 Mean | Column 7 CV |
|---|---|---|---|---|---|---|
| 2.2 | 60% | 0.154 | 0.026 | 1.25 | | |
| 2.2 | 60% | 0.162 | 0.032 | 2.71 | | |
| 4.9 | 30% | 0.066 | 0.049 | 5.21 | 5.33 | 6.83% |
| 4.9 | 30% | 0.074 | 0.047 | 5.04 | | |
| 4.9 | 30% | 0.085 | 0.052 | 5.74 | | |
| 4.9 | 45% | 0.125 | 0.044 | 4.93 | 4.97 | 0.76% |
| 4.9 | 45% | 0.126 | 0.044 | 5.00 | | |
| 4.9 | 45% | 0.130 | 0.044 | 4.99 | | |
| 4.9 | 60% | 0.167 | 0.043 | 5.88 | 5.91 | 17.11% |
| 4.9 | 60% | 0.167 | 0.040 | 4.91 | | |
| 4.9 | 60% | 0.179 | 0.043 | 6.93 | | |
| 8.1 | 30% | 0.082 | 0.066 | 7.59 | 8.20 | 10.78% |
| 8.1 | 30% | 0.086 | 0.077 | 9.21 | | |
| 8.1 | 30% | 0.075 | 0.068 | 7.80 | | |
| 8.1 | 45% | 0.130 | 0.063 | 8.42 | 8.06 | 7.83% |
| 8.1 | 45% | 0.119 | 0.059 | 7.33 | | |
| 8.1 | 45% | 0.131 | 0.062 | 8.43 | | |
| 8.1 | 60% | 0.171 | 0.051 | 8.75 | 8.08 | 7.77% |
| 8.1 | 60% | 0.161 | 0.050 | 7.50 | | |
| 8.1 | 60% | 0.165 | 0.051 | 7.98 | | |

For each sample, the Zero Optical Density (ZOD) and Delta Optical Density (DOD) are calculated from $T_{Blank}$, $T_0$ and $T_\infty$ using the formulae below;

$$ZOD = \log[(T_{Blank})/(T_0)]$$

$$DOD = [\log(T_0/T_\infty)] - ZOD$$

A series of plots of the relationship between DOD and ZOD as the haematocrit is changed for standards at the lower and upper limit of the assay working range are described mathematically using a second order polynomial curve fit. The calibration constants a, b & c (and a', b' & c') are defined (second order polynomial) for these standards of known high and low plasma cholesterol which have been manipulated to produce different haematocrit levels (see FIG. 5).

The plasma concentration of cholesterol for unknown samples can then be calculated from experimentally derived values of $DOD_{UNKNOWN}$ and $ZOD_{UNKNOWN}$ thus;

1. Calculate DOD for High Standard (H) from ZOD of sample $$DOD_{HIGH} = a \cdot ZOD^2 + b \cdot ZOD + c$$

2. Calculate DOD for Low Standard from (L) ZOD of sample $$DOD_{Low} = a' \cdot ZOD^2 + b' \cdot ZOD + c'$$

3. Calculate plasma cholesterol for unknown sample from the following expression:

$$\{[DOD_{UNKNOWN} - DOD_{LOW}]/[DOD_{HIGH} - DOD_{LOW}] \times [H-L]\} + L$$

The utility of this approach to equalising cholesterol values for the presence of red blood cells is demonstrated by back calculating the cholesterol values for the high and low standards and also of a sample which is approximately mid range between high and low standards. (Table 2; columns 5, 6 and 7 and FIG. 6.)

This shows that the derived values are largely unaffected by sample haematocrit.

What is claimed is:

1. A method of carrying out an assay for substance in a sample of whole blood, which method comprises:

(a) carrying out a reaction in solution between an analyte in the whole blood sample and a specific reagent, the sample being combined with the reagent at time $t_0$;
  (b) monitoring the transmission of the solution continuously as the reaction progresses at a suitable wavelength;
  (c) recording, from the detected transmission values, the transmission, $T_{init}$, being the transmission of the reaction solution before the addition of the sample; and calculating $T_0$, being the transmission at time $t_0$ after the sample has been added and $T_\infty$ being the transmission at time $t_\infty$, which is the point at which all of the analyte has reacted with the reagent, or has attained equilibrium;
  (d) calculating from the values of $T_{init}$ and $T_0$ the optical density of the sample after blood addition and hence quantity of haemoglobin added in that sample;
  (e) calculating from the values of $T_0$ and $T_\infty$ the change in transmission attributable to the reaction in step (a); and
  (f) deriving from the relationship between these measurements the concentration of the analyte in the sample, corrected for haematocrit variation.

2. A method as claimed in claim 1, wherein the reaction in step (a) is an immunoturbidimetric one.

3. A method as claimed in claim 2 wherein the reagent includes an antibody specific to the analyte bound to a particle.

4. A method as claimed in claim 3 wherein the particle is a latex bead.

5. A method as claimed in claim 1, wherein the analyte is C-reactive Protein.

6. A method as claimed in claim 1, wherein the reaction in step (a) is colourimetric.

7. A method as claimed in claim 6, wherein the reagent includes enzymes to produce an enzyme driven series of linked reactions to produce a coloured end point.

8. A method as claimed in claim 6 wherein the analyte is cholesterol.

9. A method as claimed in claim 6 wherein the reagent includes one or both of cholesterol oxidase and cholesterol esterase.

10. A method as claimed in claim 1 wherein the algorithm in step (f) is of the form $y = ax^2 + bx + c$, where a, b and c are calibration constants, y is a measure of analyte chemistry from the calculation of log $[(T_0-T_\infty)/T_0]$ and x is a measure of haemoglobin from the calculation of log $[(T_{init}-T_0)/T_{init}]$.

11. A method as claimed in claim 1, wherein $T_0$ is determined by back extrapolation of a curve fitted to time course transmission data, based upon the rate equation of the reaction.

12. A method as claimed in claim 1, wherein $T_\infty$ is determined by forward extrapolation of this curve fit beyond the data collection period.

13. A method as claimed in claim 11, wherein the extrapolation includes plotting the detected transmission data against time, and applying a best fit curve to the plotted points.

14. A method as claimed in claim 13, wherein the plotting is achieved by fitting a mathematical function of a curve of best fit to the data and extrapolating that function to time $t_0$ and $t_\infty$.

15. A method as claimed in claim 1 wherein the period during which transmission data is recorded is up to 3 minutes.

16. A method as claimed in claim 1, wherein before the sample is combined with the reagent in step (a), the sample alone is excited by incident electromagnetic radiation of a wavelength $\lambda_n$, wherein the wavelength $\lambda_n$ can detect both haemoglobin and the reaction and the resultant initial transmission ($T_{init}$) at the selected wavelength frequency is detected.

17. A method as claimed in claim 16, wherein $T_{init}$ in combination with the value of $T_0$ can be used to calculate the Zero Optical Density (ZOD) using the equation ZOD=Log $[T_{init}/T_0]$.

* * * * *